US005795781A

United States Patent [19]
Wille, Jr.

[11] Patent Number: 5,795,781
[45] Date of Patent: Aug. 18, 1998

[54] CELL COMPETENCY SOLUTION FOR USE IN THE FORMATION OF A HISTOLOGICALLY-COMPLETE, LIVING, HUMAN SKIN SUBSTITUTE

[75] Inventor: John Jacob Wille, Jr., Lawrenceville, N.J.

[73] Assignee: Hy-Gene, Inc., Ventura, Calif.

[21] Appl. No.: 601,717

[22] Filed: Feb. 15, 1996

Related U.S. Application Data

[63] Continuation of Ser. No. 348,569, Dec. 2, 1994, abandoned, which is a continuation of Ser. No. 63,872, May 18, 1993, abandoned, which is a continuation of Ser. No. 471,976, Jan. 29, 1990, Pat. No. 5,292,655.

[51] Int. Cl.$^6$ .................................................. C12N 5/00
[52] U.S. Cl. ........................... 435/404; 435/383; 623/15
[58] Field of Search ........................ 435/240.31, 240.3, 435/240.2, 240.21, 240.25, 404, 383; 623/15

[56] References Cited

U.S. PATENT DOCUMENTS

| | | |
|---|---|---|
| 4,757,005 | 7/1988 | Chan . |
| 4,786,599 | 11/1988 | Cheesebeuf et al. . |
| 4,851,346 | 7/1989 | Chan . |
| 4,940,666 | 7/1990 | Boyce et al. . |
| 5,152,982 | 10/1992 | Parkes et al. . |
| 5,292,655 | 3/1994 | Wille, Jr. . |
| 5,316,938 | 5/1994 | Keen et al. . |
| 5,324,656 | 6/1994 | Ham et al. . |
| 5,407,669 | 4/1995 | Lindstrom et al. . |
| 5,486,359 | 1/1996 | Caplan et al. . |
| 5,523,226 | 6/1996 | Wheeler . |
| 5,529,920 | 6/1996 | Cole et al. . |

OTHER PUBLICATIONS

Gibco Laboratories, GIBCO Laboratories Catalogue & Reference Guide, pp. 87 and 99, 1987.

*Primary Examiner*—Leon B. Lankford, Jr.
*Attorney, Agent, or Firm*—Donald O. Nickey; Standley & Gilcrest

[57] ABSTRACT

Methods and formulations are disclosed for the in vitro formation of a histologically complete human epidermis in a serum-free, companion cell or cell feeder layer-free, and organotypic matrix-free culture system commencing with the isolation and cultivation of a unique population of clonally-competent basal epidermal cells and ending with the formation of a functional, histologically complete, human squamous epithelium. The formation of a histologically complete human epidermis is accomplished in a serum-free medium, without companion-cells or feeder layer cells or any organotypic support using a multi-step process that is controlled by manipulating the growth and differentiation factors requisite to the sequential development of a usable, functional, and completely differentiated epidermis. The entire culture process can be accomplished in a relatively short time (3 to 4 weeks) with complete reproducibility and can supply copious amounts (2 to 3 square meters) of viable reformed human epidermis for a variety of experimental, clinical and commercial purposes where a histologically-complete living skin substitute is required.

7 Claims, No Drawings

CELL COMPETENCY SOLUTION FOR USE IN THE FORMATION OF A HISTOLOGICALLY-COMPLETE, LIVING, HUMAN SKIN SUBSTITUTE

This application is a continuation of Ser. No. 08/348,569 filed Dec. 2, 1994, now abandoned, which is a continuation of Ser. No. 08/063,872 filed May 18, 1993, now abandoned, which is a continuation of Ser. No. 07/471,976 filed Jan. 29, 1990, now U.S. Pat. No. 5,292,655. The teachings of U.S. Pat. No. 5,292,655 are incorporated herein by reference.

TECHNICAL FIELD OF THE INVENTION

The field of the invention is in biology and more specifically in the subspecialty of cell biology.

BACKGROUND OF THE INVENTION

The serum-free culture of normal human epidermal keratinocytes without the use of companion-cells, cell feeder layer or organotypic substrate, e.g. collagen or gelatin, is disclosed in this invention. Traditionally, tissue culture of normal epithelial cells has been attempted in a variety of commercially available media designed for the growth of less fastidious types of cells, i.e. malignant cells transformed in vitro from cell lines derived from human or nonhuman tissues, cell lines developed from human or nonhuman tumors, or cell lines developed for human or nonhuman embryonic mesenchymal cell types. In contrast, the culture of normal human epithelial stem cells has presented many difficulties not the least of which is the inexorable tendency for these cells to undergo uncontrolled, irreversible, terminal differentiation with the consequent loss of cell division capacity. A significant development which permitted the growth of human epidermal cells in culture was the formulation of a selective basal nutrient medium and its supplementation with specified growth factors and hormones (Tsao, M. C., et al., *J. Cellular Physiol.* 110:219–229 (1982)). This selective medium was designated MCDB 152. Further refinements of this medium lead to the formulation of MCDB 153 (Boyce, S. T. and Ham, R. G., *J. Invest. Dermatol.* 81:33–40 (1983)). The use of these media permitted a more accurate characterization of the necessary growth factors, hormones and $Ca^{24}$ requirements for retention of high cloning efficiency necessary to maintain proper genetic programming for continued subculture of pluripotent basal epidermal stem cells (Wille, J. J., et al., *J. Cellular Physiol.* 121:31–44 (1984)).

The actual role of serum in cell culture medium as a complex mixture of both growth factors and differentiation-inducing factors was resolved by careful clonal growth, cell division kinetics, and flow cytofluorography (Pittelkow, M. R., et al., *J. Invest. Dermatol.* 86:410–417 (1986)). These findings indicated that serum, known to contain fibroblastic cell growth factors, e.g., platelet-derived growth factor, was an inhibitor of basal epidermal cell growth. Further, the differentiation-inducing factors in serum could be equated with serum's content of β-transforming growth factor, (β-TGF), (Shipley, S. D., et al., *Cancer Res.* 46:2068–2071 (1986)). Recently, the inventor and colleagues reported that normal human keratinocytes actually produce their own growth factors. That is, proliferating basal cells are stimulated to secrete α-transforming growth factor (α-TGF) in response to the presence of added epidermal growth factor (EGF) and decrease production of α-TGF at high cell densities near confluence. Under the latter condition, the arrested cells secrete an inactive form of β-TGF (Coffen, R. J., et al., *Nature* 328:817–820 (1987)). These considerations recently led the inventor to the idea that the natural mechanism of growth stimulation and its regulation in intact epidermis involved coordinated secretions of α- and β-TGF's, and that the provision of such factors would eliminate the need for any organic substrate as well. Further experimentation to verify this surmise resulted in the findings in the present invention.

Previously, a patent (Green, H. and Kehinde, O., U.S. Pat. No. 4,304,866, 1981) was obtained for an in vitro method for the formation of epithelial sheets from cultured keratinocytes. This method uses a serum-containing medium and a feeder layer of murine (mouse) fibroblast cells to accomplish cell growth and differentiation. This procedure has serious limitations for large scale production of genetically-defined (autologous) human skin substitute. For example, the use of serum inextricably confounds the culture of purely basal cells with the dynamics of serum-induced differentiation. The net result is that subcultivation of such cultures yields low (<5%) clonal efficiencies preventing step-wise large scale build up of uncommitted pluripotent basal cells as a prelude to their conversion into usable sheets of transplantable, histologically-complete, human epidermis. Moreover, the process of Green, H. and Kehinde, O. (U.S. Pat. No. 4,304,866, 1981) does not, describe a histologically-complete epidermis. Rather, the procedures therein can only form an epidermis lacking a stratum corneum, this being necessary for maximizing the utility of the tissue, and, thus, this limits the product uses. In a more recent methodology, a complete epidermis has been achieved, but only in the presence of a complete skin starter sample and serum-containing media that are combined with an organotypic substratum containing growth factors produced by companion cells (E. Bell, U.S. Pat. No. 4,485,096, 1984; and E. Bell & L. Dubertret., U.S. Pat. No. 4,604,346, 1986). Although it is conceivable that these latter processes may be used in the absence of serum, the continued use of any organotypic substrate as well as feeder or companion cell types, e.g. fibroblasts, seriously limits, in an immunologically safe manner as well as an economic manner, their large-scale use, e.g. burn patients (Nanchahal, J., et al., *Lancet* II(8656):191–193, (1989)). In order to remedy these deficiencies the inventor has dispensed with serum-containing media, eliminated any substratum support, dispensed with the requirement for innumerable skin starter samples, and designed a new basal nutrient medium capable of supporting the growth and development of a complete epidermis. Moreover, the identification of essential process steps leading to a functional epidermis has been discovered and can be monitored with specific monoclonal antibodies. In retrospect, the culturing of epidermal keratinocytes in medium containing undefined serum and/or feeder cell factors and/or organotypic substrates, and millimolar concentrations of $Ca^{24}$ were not designed for the unlimited proliferation of undifferentiated basal cells. Such cultures can spontaneously undergo maturation and uncontrolled differentiation. The result was that an incomplete epidermis was produced. By contrast, the design of serum-free culture process described in this invention produces a complete epidermis i.e. an epidermis which is formed of all six major identifiable layers of a complete human epidermis by an orderly sequence at will, from a defined starting point in the culture process.

SUMMARY OF THE INVENTION

There is disclosed the design and formulation of the novel HECK-109 mediums which have been differently supplemented to provide for the serial achievement of the three-step cellular differentiation process of pluripotent basal cell keratinocytes to a fully differentiated human skin in vitro: i) HECK-109, the basal medium for cell starting; ii) HECK-109 fully-supplemented medium (hereinafter referred to as HECK-109FS) for control over cellular growth; iii) HECK-109-differentiation medium (hereinafter referred to HECK-109DM) for the induction of differentiation and formation of a Malpighian layer; and iv) HECK-109-cornification medium (hereinafter referred to HECK-109CM) designed for the induction of cellular differentiation of a stratum lucidum, stratum corneum, and stratum disjunction in a pre-existing reformed epidermis produced by HECK-109DM. The entire system involves the matter of the sequential rendering of the culture process steps and the method of sequential control in the in vitro construction of a histologically-complete living skin substitute in a totallly serum-free medium, feeder layer-free, and matrix-free (collagen or other organotypic matrix) process.

This disclosure includes: I a nutrient basal medium designated HECK-109. The critical component concentrations incorporated into this medium design are about: i) N-(2-OH-ethyl-) piperazine-N'-(2-ethanesulfonic acid) (hereinafter referred to as HEPES) at 14–22 mM; ii) NaCl at 90–140 mM; iii) low $Ca^{2+}$ level at 0.03–0.3 mM; and iv) six key amino acids of Stock 1 of HECK-109 (SEE: TABLE 1) set at about the following concentrations. Histidine= $1.0-2.5\times10^{-4}M$; Isoleucine=$0.5-5.0\times10^{-4}M$; Methionine= $1.0-5.0\times10^{-4}M$; Phenylalanine=$1.0-5.0\times10^{-4}M$; Tryptophan=$0.5-5.0\times10^{-4}M$; and Tyrosine=$1.0-5.0\times10^{-4}M$. Taken together, HEPES, NaCl, and the six key amino acids are critically superior to any previous media or similar design, in toxicity, osmolarity, and support of clonal growth of basal epidermal cells; II a growth medium for undifferentiated basal keratinocytes based on HECK-109 basal medium and herein designated HECK-109FS. This medium consists of basal nutrient medium HECK-109 supplemented at about the following levels: $Ca^{2+}$ =0.03–0.30 mM; hydrocortisone=$1.0-5.0\times10^{-7}M$; phosphoethanolamine= $0.5-2.0\times10^{-4}M$; ethanolamine=$0.5-2.0\times10^{-4}M$; epidermal growth factor (EGF)=1–25 ng/ml; insulin-like growth factor-1 (IGF-1)=0.3–30 ng/ml; and soy bean trypsin inhibitor (SOTI;=0.1–1.0% w/v). This medium is selective for the growth of normal human epidermal keratinocytes and is essential for Phase I of the culture growth in that it supports the formation of a hole-free monolayer of undifferentiated keratinocytes while suppressing growth-arrest and any significant decline in clonogenic potential. These properties are unlike any previous media used to support proliferation of basal keratinocytes. The key features of HECK-109FS which make it different and superior to all other keratinocyte growth media are the use of IGF-1 and EGF as the only two protein growth factors used in conjunction with low $Ca^{2+}$ (0.03–0.30 mM); III a cytodifferentiating growth medium based on basal HECK-109 medium and herein designated HECK-109DM. As detailed in the disclosure, Example 4, the induction of synchronous growth arrest, commitment to terminal keratinocyte differentiation, and formation of a supra-basal cell layer superimposed on top of a proliferation-competent basal cell layer is achieved by replacement of HECK-109FS with HECK-109DM. The latter medium is composed of HECK-109 basal medium supplemented at about the following levels: $Ca^{2+}$ =0.7–3.0 mM; hydrocortisone=$1-10\times10^{-7}M$; phosphoethanolamine= $0.5-2.0\times10^{-4}M$; ethanolamine=$0.5-2.0\times10^{-4}M$; EGF=1–5 ng/ml; IGF-1=0.3–30.0 ng/ml; and β-transforming growth factor (β-TGF)=3–30 ng/ml. Addition of β-TGF is a key required to arrest basal keratinocytes through a pathway that prepares the monolayer for induction of stratification, a step under the joint control of EGF (1–5 ng/ml), β-TGF (3–30 ng/ml), and $Ca^{2+}$ (0.7–3.0 mM). HECK-109DM must be replaced by HECK-109CM (Cornification-inducing Medium) to achieve the final steps in the induction of a full-thickness, histologically-complete epidermis; IV a differentiation and cornification medium based on basal HECK-109 medium and herein designated HECK-109CM. This medium is designed to induce the competent formation of a stratum corneum, which also leads to the appearance of a stratum lucidum and stratum disjunction. HECK-109CM is based on HECK-109 basal medium and has about the following levels of critical components which achieve this step (in addition to HECK-109 basal medium): linoleic acid=1–15 µg/ml; hydrocortisone=$1.0-10.0\times10^{-9}M$; phosphoethanolamine=$0.5-2.0\times10^{-4}M$; ethanolamine= $0.5-2.0\times10^{-4}M$; and $Ca^{2+}$ =0.7–3.0 mM; V a method, including design and formulation of a cell competency solution (herein designated CCS), whereby clonally competent basal keratinocytes are isolated from human skin samples by the procedures outlined in Example 1. The essence of these steps is the recovery of a unique subpopulation of basal cells which differ from basal cells tightly associated with the dermis. Separation versus tight association is defined as those cells (the unique disassociated subpopulation) which are recovered from treatment of a human skin biopsy with 0.1–0.2 percent trypsin (w/v) dissolved in CCS. CCS is designed to permit the initial isolation of a subpopulation of clonally competent basal keratinocytes that retain a high clonality, in other words, retain an unrestricted division potential and be fully competent to undergo differentiation. This is due to the low toxicity of this medium and improved osmolality which differ from all other isolation solutions for such cells. The approximate composition of CCS is as follows: glucose=10 mM; KCl=3 mM; NaCl=90–140 mM; $Na_2HPO_4.7H_2O$=1 mM; phenol red= 0.0033 mM; HEPES=16–22 mM; 100 Units per ml both of penicillin and streptomycin and SOTI=0.1–1.0 percent (w/v). The isolated subpopulation of competent basal cells are then seeded into HECK-109FS at $5\times10^4$ cells/$cm^2$ and are clonally amplified to the density of $2\times10^4$ to $2\times10^5$ cells/$cm^2$ prior to their serial passage into secondary culture, and the clonal growth of said cells; and VI a method wherein the requirements for the preparation and sequential differentiation of a secondary proliferating monolayer of undifferentiated or differentiated keratinocytes are outlined (referred to as Phases I, II, and III). Said procedures include the seeding of clonally competent keratinocytes into HECK-109FS at an initial cell density of about $5\times10^2$ to $3\times10^3$ cells/$cm^2$ and their growth to a density of about $2-4\times10^5$ cell/$cm^2$ prior to the induction of differentiation (Phase I) and sequential formation of a histologically-complete stratified epithelium by the controlled progressive and sequential culture of the cells in HECK-109DM (Phase II), and HECK-109CM (Phase III) wherein the final in vitro skin product contains all layers of a histologically complete epidermis.

The above description discloses a process that is premised upon the realization that a viable, and completely reformed human epidermis with a stratum corneum can be entirely reformed in culture by following an orderly sequence of steps hitherto unknown whereby these steps are absent serum, feeder cells or organotypic substrates of any type. Phase I is the culturing of primary normal human keratinocytes in a newly designed serum-free medium (Medium HECK-109). Although the usual procedure for obtaining keratinocytes involves foreskins, adult skin specimens from virtually any body site and of at least 1 to 2 cm² (such as a punch biopsy) provides a sufficient number of input cells to start a primary culture. Phase I is capable of amplifying the initial input of cells of the epidermis by a factor of 100,000 by serial subcultivation procedures (secondary cultures), requires less than two weeks, and provides enough basal cells to eventually form about 2 to 3 square meters of histologically complete and viable epidermis. Once secondary cultures of basal cells have been amplified in Phase I to the desired extent, the proliferating cultures are stimulated to reach confluence and form a hole-free sheet in the presence of a medium designed to ensure retention of undiminished clonal growth. This supplementation step is crucial. It is achieved by replacing the basal HECK-109 serum-free culture medium with HECK-109 medium enriched in specific amino acids outlined above and linoleic acid. In this latter medium, the basal cells within the monolayer continue to proliferate resulting in the formation of a crowded monolayer, with continued clonal growth capacity until used in Phase II in the process.

Phase II in the cell culture process is the induction of identifiable cell strata with the formation of a nondividing suprabasal cell layer, and continued proliferation of the underlying basal cells. These events are simultaneously induced by replacement of the second-step HECK-109 enrichment medium with the basal HECK-109 serum-free medium containing β-TGF (3 to 30 ng per ml), and $Ca^{2+}$ (0.7 to 3.0 mM). This medium additionally lacks EGF and IGF-1. Within a few days, the proliferating cell monolayer converts into a stratified epidermis, which then progressively thickens to form a multilayered living sheet of epidermis. This process continues for about a week in culture and completes Phase II of in vitro formation of a human epidermis.

At this stage, the epidermis consists of three histologically recognizable and antibody-identifiable cell layers, a bottom-most basal cell layer (stratum germinativum), a spinous cell layer (stratum spinosum) above it, and a top-most granular cell layer (stratum granolosum), but no formation of a cornified stratum (stratum corneum), or bordering layers, e.g. stratum lucidum and stratum disjunction. This development requires a third phase of culture. The second phase culture, characterized by an incomplete epidermis, will persist in culture for an extended period (>30 days). It will, however, lose the capacity to convert to a complete epidermis. This is prevented by initiation of Phase III of culture. The second phase medium is replaced with a first-phase serum-free medium that lacks all added protein growth factors but has elevated $Ca^{2+}$ (0.7–3.0 mM) and linoleic acid (1–15 µg/ml) in the medium.

Unlike the characterization of all existing methods and processes the construction of a completely reformed human epidermis in the above manner is vastly superior to any method employing serum-containing media and/or feeder layer support and/or organotypic matrices because it is faster, reproducible and provides a uniform composition to the finished product from an autologous source. It also affords the possibility of intervening at any of the crucial steps in the process in ways that might augment the cellular content of one of the living versus nonliving cell layers. Finally, the ease of amplifying the initial input through rapid serial cell culture makes this the choice method for instituting autografts within the framework of the time constraints operative during therapeutically-assisted recovery of severe burn patients besides being a long term solution in this and other wound healing problems.

DETAILED DESCRIPTION OF THE INVENTION

EXAMPLE 1

Primary and Secondary Culture of Normal Human Epidermal Keratinocytes in HECK-109 Serum-Free Medium Isolation of Basal Cells and Primary Cultures Through extensive experimentation, I have developed HECK-109, a new serum-free medium, and developed methods detailed below for the successful propagation of normal human basal epidermal keratinocytes from either newborn or adult skin. Primary cultures of normal human basal epidermal keratinocytes are started by subjecting full-thickness skin samples to enzymatic digestion. Skin obtained from biopsies or autopsies is first cleaned of adhering subdermal fat and the dermis is reduced to less than 3 mm in thickness. The skin sample is then typically cut into 8 to 12 small pieces (usually 0.5 cm²). These pieces are floated on top of a sterile Cell Competency Solution (CCS). The formula for CCS is as follows: glucose, 10 mM; KCl, 3 mM; NaCl, 90–140 mM; $Na_2HPO_4.7H_2O$, 1 mM; phenol red, 3.3 µM; and HEPES at 14–22 mM. (SEE: Shipley, G. D. and Ham, R. G., In Vitro 17:656–670 (1981)). 0.10–0.20 percent trypsin (w/v), and 100 units/ml of both of the antibiotics penicillin and streptomycin. After 14 to 16 hours of digestion at 4° C. the dermis is separated from the epidermis by a split-dermis technique. This is accomplished by inverting the skin sample, i.e., by placing the cornified layer side of the epidermis onto a clean sterile polystyrene surface, as accomplished by existing typical techniques. The epidermis spontaneously detaches, and the dermis is removed with sterile forceps. I have shown that trypsin digestion cleaves the skin along a fracture line which separates some of the basal cells with the dermis, but frees other basal cells lying between the dermis and the fracture line just above the basal cell layer.

The trypsin-treated epidermis, so split from the dermis, is enriched for a subpopulation of loosely-associated, clonally competent basal cells. In a series of experiments, I discovered that these loosely-associated basal cells are larger than the basal cells that remain associated with the dermis. Moreover, these larger basal cells are separable by cell sorting procedures using a florescence-activated cell sorting device. They also have a greater colony-forming ability than the dermis-associated basal cells, as demonstrated by clonal growth experiments.

The loosely-associated basal cells are collected in ice-cold (0° to 4° C.) CCS containing 0.1–1.0 percent w/v SOTI solution as outlined above, and the cell suspension filtered on ice through a 100 micrometer sized Nylon mesh by sterile procedures. Filtration removes cell aggregates and ensures preparation of a single cell suspension. The cells are pelleted by low speed centrifugation (800×grav, 5 minutes) at 4° C. The above solution is aspirated off and the remaining cells are resuspended by gentle pipetting in CCS, and washed once with ice-cold, serum-free basal nutrient medium (here designated HECK-109; see Example 2 for detailed composition of this medium). The centrifugation step is repeated as above, and the resulting cell pellet is resuspended in 1 to 2 ml of fresh HECK-109 medium. Cell counts are obtained by standard cell chamber counting methods. Primary cultures are initiated into HECK-109 medium supplemented with 0.1 (0.05–0.20) mM ethanolamine; 0.1 (0.05–0.20) mM phosphoethanolamine; 0.5 (0.1–1.0) µM hydrocortisone; 0.2 percent (0.1–1.0) of SOTI, w/v. Antibiotics which are added at this time can be removed 2 to 3 days later when the proliferating cell cultures are refed fresh complete medium. The complete growth medium (HECK-109FS) is further supplemented with 10 ng/ml EGF (1–25 ng/ml), and 5 µg/ml IGF-1 (0.3–30 ng/ml). The latter two protein growth factors are added aseptically to the medium. Other medium supplements and media with the above supplements are sterilized through a commercially available membrane filter. The initial seeding density for initiating the primary culture is $5 \times 10^4$ basal cells per 75 $cm^2$ tissue culture flask. Generally, two such flasks are routinely set up from an initial yield of 1 to $2 \times 10^6$ cells isolated from a 1 to 2 $cm^2$ piece of skin.

Secondary Culture Procedure

Secondary cultures initiated from either primary cultures or early passage secondary cultures are passaged by enzymatic dissociation of cells. This serial passage technique is not standard. It involves the use of ice-cold 0.02 (0.02–0.20) percent trypsin (w/v) and 0.1 (0.08–0.12) percent ethylenediaminetetraacetic acid (EDTA; w/v) dissolved in CCS to remove the cells from their plastic substrate. The cells are collected in ice-cold 0.2 (0.1–1.0) percent SOTI (w/v) in CCS as detailed above for initiating primary cultures. Typically, secondary cultures are seeded at an initial cell density at a 1000 cells per $cm^2$, but lower seeding densities are possible.

The procedures for calculating colony forming efficiency (CFE) of the basal cells recovered from the epidermis and used to initiate a primary culture is to set up duplicate primary cultures at 5000 cells per $cm^2$ as described above, and then to count the number of cells which attach and which later form a colony of at least 8 or more cells three days after seeding the primary culture. By this method, the percent attachment of epidermal cells is 50 to 60 percent of the input cells. The colony forming efficiency ranges between 0.1 to 0.5 percent of the input cells as measured by ocular micrometer grid square counts on living cultures.

EXAMPLE 2

Preparation of HECK-109 Basal Nutrient Medium

Some of the novel methods and materials provided by the invention relate to the preparation of a new basal nutrient medium suitable for the large scale amplification of both primary and secondary cultures of normal human keratinocytes, and for conversion of proliferating normal human keratinocyte monolayer cultures to a stratified squamous epithelium applicable to a transplantable skin equivalent. More particularly, Example 2 is directed to the materials and procedures for preparation of a basal nutrient medium (Human Epidermal Cell Keratinocyte, HECK-109), and evidence for its superiority in stimulating epidermal growth by design of the osmolarity, toxicity, and pH-buffering properties of the standard basal medium formulation.

Table I, below, details the concentration of components in basal medium, HECK-109. All biochemicals and hormones are from Sigma Chemical Company (St. Louis, Mo., U.S.A.), and all inorganic chemicals are from Fisher Scientific (Pittsburgh, Pa., U.S.A.). All trace elements in Stock T are from Aesor (Johnson Matthey, Inc., Seabrook, N.H., U.S.A., Purotronic Grade). EGF may be prepared according to the procedure of Savage, R. C. and Cohen, S. (*J. Biol. Chem.* 247:7609–7611 (1972)), or purchased from Collaborative Research, Inc., Waltham, Mass.

One liter of HECK-109 is prepared in a separate stock solution fashion as described in Table I with respect to Stocks 2 through 10. Medium HECK-109 differs from all other media in the prior art by its Stock 1 amino acids, its concentration of NaCl (113 mM; Range 90–140) and of HEPES (20 mM; Range 14–22). The design of the level of amino acids must include the following 6 amino acids: Isoleucine=$0.5–5.0 \times 10^{-4}$M; Histidine=$0.5–2.5 \times 10^{-4}$M; Methionine=$1.0–5.0 \times 10^{-4}$M; Phenylalanine=$1.0–5.0 \times 10^{-4}$M; Tryptophan=$0.5–5.0 \times 10^{-4}$M; Tyrosine=$1.0–5.0 \times 10^{-4}$M.

TABLE I

Composition of Basal Nutrient Medium HECK-109

| Stock | Component | Concentration in final medium mg/l | mol/l* |
|---|---|---|---|
| 1 | Arginine.HCl | 421.4 | $2.00 \times 10^{-3}$ |
|  | Histidine.HCl.H$_2$O | 36.1 | $1.70 \times 10^{-4}$ |
|  | Isoleucine allo-free | 33.0 | $2.50 \times 10^{-4}$ |
|  | Leucine | 132.0 | $1.00 \times 10^{-3}$ |
|  | Lysine.HCl | 36.6 | $2.00 \times 10^{-4}$ |
|  | Methionine | 45.0 | $3.00 \times 10^{-4}$ |
|  | Phenylalanine | 50.0 | $3.00 \times 10^{-4}$ |
|  | Threonine | 23.8 | $2.00 \times 10^{-4}$ |
|  | Tryptophan | 40.8 | $2.00 \times 10^{-4}$ |
|  | Tyrosine | 54.0 | $3.00 \times 10^{-4}$ |
|  | Valine | 70.2 | $6.00 \times 10^{-4}$ |
|  | Choline | 20.8 | $2.00 \times 10^{-4}$ |
|  | Serine | 126.1 | $1.20 \times 10^{-3}$ |
| 2 | Biotin | 0.0146 | $6.00 \times 10^{-8}$ |
|  | Calcium Pantothenate | 0.285 | $1.00 \times 10^{-6}$ |
|  | Niacinamide | 0.03363 | $3.00 \times 10^{-7}$ |
|  | Pyridoxal.HCl | 0.06171 | $3.00 \times 10^{-7}$ |
|  | Thiamine.HCl | 0.3373 | $1.00 \times 10^{-6}$ |
|  | Potassium chloride | 111.83 | $1.50 \times 10^{-3}$ |
| 3 | Folic acid | 0.79 | $1.80 \times 10^{-6}$ |
|  | Na$_2$HPO$_4$.7H$_2$O | 536.2 | $2.00 \times 10^{-3}$ |
| 4a | Calcium chloride.2H$_2$O | 14.7 | $1.00 \times 10^{-4}$ |
| 4b | Magnesium chloride.6H$_2$O | 122.0 | $6.00 \times 10^{-4}$ |
| 4c | Ferrous sulfate.7H$_2$O | 1.30 | $5.00 \times 10^{-6}$ |
| 5 | Phenol red | 1.242 | $3.30 \times 10^{-6}$ |
| 6a | Glutamine | 877.2 | $6.00 \times 10^{-3}$ |
| 6b | Sodium pyruvate | 55.0 | $5.00 \times 10^{-4}$ |
| 6c | Riboflavin | 0.03764 | $1.00 \times 10^{-7}$ |
| 7 | Cysteine.HCl | 37.6 | $2.40 \times 10^{-4}$ |
| 8 | Asparagine | 13.2 | $1.00 \times 10^{-4}$ |
|  | Proline | 34.53 | $3.00 \times 10^{-4}$ |
|  | Putrescine | 0.1611 | $1.00 \times 10^{-6}$ |
|  | Vitamin B$_{12}$ | 0.407 | $3.00 \times 10^{-7}$ |
| 9 | Alanine | 8.91 | $1.00 \times 10^{-4}$ |
|  | Aspartic acid | 3.99 | $3.00 \times 10^{-5}$ |
|  | Glutamic acid | 14.71 | $1.00 \times 10^{-4}$ |
|  | Glycine | 7.51 | $1.00 \times 10^{-4}$ |
| 10 | Adenine | 12.16 | $9.00 \times 10^{-5}$ |
|  | Inositol | 18.02 | $1.00 \times 10^{-4}$ |
|  | Lipoic acid | 0.2063 | $1.00 \times 10^{-6}$ |
|  | Thymidine | 0.7266 | $3.00 \times 10^{-6}$ |
| Trace element | Copper sulfate.5H$_2$O | 0.00025 | $1.00 \times 10^{-9}$ |
|  | Selenic acid | 0.00387 | $3.00 \times 10^{-8}$ |
| T | Magnesium sulfate.5H$_2$O | 0.00024 | $1.00 \times 10^{-9}$ |
|  | Sodium silicate.9H$_2$O | 0.1421 | $5.00 \times 10^{-7}$ |
|  | Ammonium molybdate.4H$_2$O | 0.00124 | $1.00 \times 10^{-9}$ |
|  | Ammonium vanadate | 0.00059 | $5.00 \times 10^{-9}$ |
|  | Nickel chloride.6H$_2$O | 0.00012 | $5.00 \times 10^{-10}$ |
|  | Stannous chloride.2H$_2$O | 0.000113 | $5.00 \times 10^{-10}$ |
|  | Zinc chloride.7H$_2$O | 0.1438 | $5.00 \times 10^{-7}$ |
| Solids | Glucose | 1081.0 | $6.00 \times 10^{-3}$ |
| S | Sodium acetate.3H$_2$O | 500.0 | $3.70 \times 10^{-3}$ |
|  | Sodium bicarbonate | 1176.0 | $1.40 \times 10^{-2}$ |
|  | Sodium chloride | 6600.0 | $1.13 \times 10^{-2}$ |
|  | HEPES | 4700.0 | $2.00 \times 10^{-2}$ |

*All above components come together to a final volume of 1 liter of distilled and 0.22 µm-filtered water.

The indicated concentrations of these 6 amino acids have been shown by the inventor to be necessary for sustained basal cell proliferation. By further experimentation, the inventor showed that superior growth occurs when the osmolarity of the basal nutrient medium is 300 (275–325) milliosmoles (mOsM). Finally, through an extensive series of clonal growth experiments in which the osmolarity was held constant at 300 mOsM and the concentration of HEPES varied between 14 to 28 mM it was discovered that the design of HECK-109 must incorporate HEPES at 20 mM (14–22 mM); this is critical to its function with the other ingredients. Table II presents typical results of clonal growth experiments showing that the design of HECK-109 supports a higher growth rate and a higher colony forming efficiency than a standard MCDB 153 commercial medium.

At this point, I wish to stress those novel aspects of the HECK-109 basal nutrient medium and, to discuss subsequent discoveries. The most significant discovery is that the concentration of HEPES (20 mM) in HECK 109 medium results in a 2 to 3 fold higher colony forming efficiency than that previously attainable. The second discovery is that an osmolarity of 300 mOsM of the medium permits attainment of higher saturation densities at confluence of monolayer culture. The third discovery is that it is necessary to provide the indicated concentrations of 6 key amino acids present in Stock 1 (2 to 5 times higher concentration than that in commercially available in MCDB 153 medium). This allows normal human keratinocyte cultures to routinely achieve a cell density equal to or greater than 100,000 cells per $cm^2$. Media HECK-109 incorporates these three discoveries in such a way that the newly designed formulation will now fully support the formation of a complete reformed human epidermis as detailed below.

TABLE II

Effect of Osmolarity and HEPES Concentrations on the Growth Response of Normal Human Keratinocytes

| Culture media | HEPES (mM) | NaCl (mM) | Osmolarity (mOsM) | Growth Response (Colonies/dish) | |
|---|---|---|---|---|---|
| | | | | AHK[a] | NHK[b] |
| MCDB-153 | 28 | 130 | 340 | 84 ± 12 | 275 ± 24 |
| HECK-109 | 23 | 104 | 300 | 196 ± 23 | 438 ± 35 |

[a]Secondary cultures of adult skin normal human keratinocytes (AHK) were seeded at 2 × 10³ cells/dish in MCDB 153 medium, and refed HECK-109 48 hours later. Dishes were fixed for colony counts 6 days later.
[b]Clonal growth experiments were performed on neonatal foreskin secondary normal human keratinocytes (NHK) cultures as described in Wille, J. J., et al., J. Cellular Physiol. 121:31–44 (1984).

EXAMPLE 3

Clonal Growth Studies Employing Single Cell Clones in HECK-109 Medium

Normal human keratinocyte cultures were routinely initiated, from either foreskin or adult female breast skin, as detailed above in Example 1, and then placed into secondary culture in complete HECK-109FS medium. The purpose of the following experiment was to determine the colony forming ability of individual keratinocyte stem cells obtained from different skin donors and from different passage levels of the same normal human keratinocyte sample. It is stressed here that each culture was established from a single genetic source to ensure that the responses observed represent only deliberate experimental manipulations. The technique of cloning individual cells was accomplished by seeding 1000 cells from a exponentially dividing parent culture into a 100 $mm^2$ Petri dish containing prewarmed HECK-109FS medium. The dish had been preseeded with a large number of sterile cloning chips (0.4 $cm^2$, Bellco Glass Company, Vineland, N.J., U.S.A.). Individual glass chips were screened microscopically with an inverted phase contrast microscope and only those bearing a single cell were selected and placed into a sterile 35 $cm^2$ petri dish and refed fresh HECK-109FS medium. Visual observations of each such single cell isolate were made and a daily record of the number of cells formed from each single-celled clone. The results of these experiments are as set forth in Tables III and IV. The data show that each proliferating basal cell from a given donor culture has an exceedingly high clonogenic potential.

Typically, a clone is comprised of more than 1000 cells, indicating that the original single cell had undergone more than 10 doublings. Such clones are, by definition, basal stem cells and data on their clonal analysis is presented in Tables III and IV. The results in Table III show that 70 percent of single cells derived from a third passage neonatal foreskin normal human keratinocyte cultures were, in fact, keratinocyte stem cells. Adult-derived normal human keratinocyte secondary cultures also at the third passage level had a significantly reduced clonogenic potential (48 percent), which correlates with the slower growth rate (48 hour doubling time) of the parent culture, which when compared with the rapid (24 hour doubling time) of the neonatal foreskin normal human keratinocyte culture clearly shows that the proliferative potential of stem cells is determined by prior culture conditions. Table IV presents data comparing five different neonatal foreskin normal human keratinocyte cultures and shows again, the fact that a consistently high clonogenic potential is maintained in secondary cultures under prior culture conditions.

TABLE III

Comparison of the Proliferative Potential of Individual Adult Versus Neonatal Keratinocyte Basal Cells Prior Culture Culture Condition[a,b]

| Clone No. Clones (N) | Passage No. | Density ($10^4/cm^2$) | Average GT (hrs) | % Proliferative |
|---|---|---|---|---|
| Adult (109) | 3 | 0.4 | 48 | 48 |
| Neonatal (106) | 3 | 7.5 | 24 | 70 |

[a]GT is defined as the average population doubling time (in hours) of the culture.
[b]N is the number of single cell clones tested.

TABLE IV

Clonal Analysis of the Proliferative Potential of Individual Keratinocyte Basal Cells Prior Culture Condition[a,b]

| Neonatal Clone No. | Passage level | Cell density ($10^4/cm^2$) | Average GT (hr) | % Proliferative Clones (N) |
|---|---|---|---|---|
| 1 | 2 | 1.87 | 24 (5)[c] | 75 (32) |
| 1 | 3 | 1.73 | 24 (6) | 66 (35) |
| 2 | 2 | 1.0 | 24 (4) | 79 (34) |
| 3 | 2 | 1.1 | 24 (6) | 68 (37) |
| 4 | 2 | 0.65 | 30 (4) | 51 (93) |
| Mean % = | | | | 63 (231) |

[a]GT is defined as the average population doubling time (in hours) of the culture.
[b]N is the number of single cell colonies tested.
[c]The number in parentheses within this column indicates the age of the parent culture in days.

In summary, the combined results of 231 single cells cloned at random from secondary cultures reared IN HECK-109FS medium showed that at least 63 percent were keratinocyte stem cells. The results of these single cell clonal studies indicate that the novel basal medium HECK-109 supports increased clonal growth of basal cells and enhances their clonogenic potential 10 times above the reported values obtained by Green, H. and Rheinwald, J. (U.S. Pat. No. 4,016,036, 1980) or in the serum-free culturing process of Boyce, S. T. and Ham, R. G. (U.S. Pat. No. 4,673,649, 1986). These considerations are of utmost relevance to the claims of this patent and for the purpose of obtaining a commercially usable in vitro manufactured living skin substitute.

EXAMPLE 4

Steps for the Formation of a Complete Epidermis in the Serum-Free HECK-109 Culture Medium The formation of a complete reformed human epidermis in serum-free HECK-109 medium is accomplished in three separate culture phases. Phase I of culture begins with the seeding of basal keratinocyte stem cells into culture dishes (the number and size of the culture dishes is only limited by the absolute number of cells obtained in the preceding normal human keratinocyte early passage culture) at a cell density of approximately a 1000 cells per $cm^2$. Typically, several million keratinocyte stem cells can be prepared from a single primary culture flask, representing about a 5000-fold increase in cells over the starting stem cells recovered from the skin sample. All normal human keratinocyte cultures are fed complete HECK-109FS medium, i.e., basal HECK-109 supplemented with phosphoethanolamine=0.1 mM (0.05–0.20); ethanolamine=0.1 mM (0.05–0.20); hydrocortisone=0.5 µM (0.1–1.0); EGF=10 ng/ml (1–25); IGF-1=5 ng/ml (0.3–30.0). Cultures are refed fresh medium every other day until the cell density equals 1 to $2\times10^4$ cells per $cm^2$. The cultures are then refed HECK-109FS medium containing the following six key amino acids: Histidine=1.7 $(0.5-2.5)\times10^{-4}$M; Isoleucine=2.5 $(0.5-5.0)\times10^{-4}$M; Methionine=3.0 $(1.0-5.0)\times10^{-4}$M; Phenylalanine=3.0 $(1.0-5.0)\times10^{-4}$M; Tryptophan=2.0 $(0.5-5.0)\times10^{-4}$M; and Tyrosine=3.0 $(1.0-5.0)\times10^{-4}$M. Cultures refed this medium every other day routinely reach confluence in 6 to 10 days.

Phase II, the induction of the stratum spinosum and the stratum granulosum and concomitant maintenance of the stratum germinativum, begins with the removal of the amino acid-enriched HECK-109FS medium and its replacement with complete amino acid-enriched HECK-109DM medium containing 0.7 to 5 mM $Ca^{2+}$ and β-TGF (3 to 30 ng/ml). This treatment in low density culture results in a parasynchronous growth arrest in the $G_1$ phase of the cell cycle (Shipley, G. D., et al., Cancer Res. 46:2068–2071 (1986) and Wilke, M., et al., Amer. J. Pathol. 131:171–181 (1988)). However, the addition of β-TGF to proliferating monolayer cultures which have attained confluence and which are still dividing, induces, within 48–96 hr, a progressive stratification of the basal cells to form a multilayered epithelium. Concomitantly, the clonogenic potential of the culture declines to approximately 50 percent. By the combined addition of β-TGF, and EGF, a fraction of the dividing basal cells is repressed, and the remaining basal cells, which have already entered into the succeeding cell cycle, are committed to form suprabasal cells. The latter progressively enlarge, differentiate into cell types representative of the spinous and granular cell layers, and migrate to the upper layers of the multilayered epidermis where they are shed into the medium. The result of this differentiation process is the formation of an extended sheet of multilayered epidermis. This process takes several days to a week to complete, and results in an incomplete living epidermis comprised of a basal cell layer with an overlying Malpighiian cell layer stratum germinativum+stratum spinosum).

The final step of the of culture process (Phase III) converts the incomplete epidermis to a complete human epidermis by induction in the uppermost layers of a cornified cell layer [stratum lucidum, stratum corneum] and stratum disjunction. This step is accomplished by removal of the amino acid-enriched HECK-109DM medium containing β-TGF, EGF and 0.7 to 5 mM $Ca^{2+}$ and its replacement with HECK-109CM, i.e. amino acid-enriched basal HECK-109 medium supplemented with 0.7 or 5 mM $Ca^{2+}$, 5 µg linoleic acid (1–15 µg/ml); 0.1 mM phosphoethanolamine (0.05–0.20 mM); 0.1 mM ethanolamine (0.05–0.20 mM); and 0.5 µM hydrocortisone (0.1–1.0 µM). During Phase III of culture, granular cells continue to mature into cornified, anucleate cells which form the topmost layer of the completed epidermis.

EXAMPLE 5

Applications of Reformed Human Epidermis as a Living Skin Substitute

From previous studies in the literature it is widely known that human skin is a target organ for certain sex steroid hormones. In fact, skin is the next most active site after the liver for the metabolic interconversions of steroid hormones. Nevertheless, little is known about the direct effect of sex steroid hormones such as testosterone, progesterone and estrogens on the growth and differentiation of normal human keratinocytes.

A. Effect of Sex Steroid Hormones on Basal Epidermal Cells Cultured in Serum-Free Medium.

It has been reported (Peehl, D. M. and Ham, R. G., In Vitro 16:516–525 (1980)) that 17-β-estradiol stimulated the growth of epidermal cells in culture. However, the stimulatory effect that was observed was minimal and occurred under less than optimal clonal growth conditions. To whit, the medium employed and the growth factors present in that medium were not the media in which serum-free growth occurs under completely defined conditions. In view of these considerations, and because living skin substitutes are an ideal model for assaying the effects of sex steroid hormones it was important to reassess the effects of sex steroid hormones in HECK-109 medium containing only defined components and supplements. This example (5A) details my findings of the effect of testosterone, progesterone, 17-β-estradiol on the clonal growth of normal human keratinocytes in HECK-109FS. Table V present results which show that both progesterone ($3.7\times10^{-6}$M) and 17-β-estradiol ($3.4\times10^{-6}$M) exert an inhibitory action on the proliferation of basal keratinocyte stem cells derived from either newborn foreskin or adult breast skin. By contrast, testosterone ($3.7\times10^{-6}$M) has only a negligible effect on the clonal growth of these cells. Further, the results show that female-derived keratinocytes are less sensitive to the inhibitory effect of the female sex steroid hormones than are the male-derived keratinocytes (provided that the keratinocytes derived from adult skin are also for some unknown reason less sensitive than newborn). The above results imply that the normal pathways regulating keratinocyte proliferation may be profoundly perturbed by continuous exposure to progesterone or progesterone-related steroids, and therefore, these effects may need to be taken into account where reformed human epidermis is used as a model for the transdermal delivery of contraceptive steroids.

TABLE V

Effect of Estradiol Progesterone, and Testosterone on Clonal Growth of Normal Human Basal Keratinocytes

| Culture conditions | Growth Responses[a] (colonies/dish) | |
|---|---|---|
|  | AH[b] | NF[c] |
| HECK-109FS medium | 569 | 286 |
|  | 585 | 312 |
| +Testosterone | 603 | 259 |
| (1.0 µg/ml) | 583 | 264 |
| +Progesterone | 311 | 58 |
| (1.0 µg/ml) | 402 | 26 |
| +Estradiol | 426 | 83 |
| (1.0 µg/ml) | 363 | 58 |

[a]Values represent the results of duplicate determinations.
[b]AH, adult skin keratinocytes were seeded at a density of 1000 cells per dish; the dishes were fixed and counted 10 days later.
[c]NF, foreskin keratinocytes were seeded at a density of 500 cells per dish; the dishes were fixed and counted 10 days later.

B. Demonstration of Specific and Saturable 17-β-estradiol Receptors in Reformed Human Epidermis.

Human epidermis reformed in serum-free culture by the process steps outlined above can be used as a model system to assay the affect of a wide variety of test substances, e.g., hormones, toxins, viruses and carcinogens. Of immediate interest for the use of reformed human epidermis as a living skin substitute for transdermal delivery of contraceptive hormones is the question of whether reformed human epidermis has specific and saturable sex steroid hormone binding sites.

This example (5B) presents a series of experiments to measure the binding of radiolabelled 17-β-estradiol to replicate samples of human epidermis from a single genetic source. Reformed human epidermis was produced by culturing basal keratinocytes as outlined in Example 2 in replicate 24-well cluster dishes (Corning Tissue Culture Wares, Corning, N.Y.) through Phase III of culture. Several test wells were sampled at the time of the binding experiments by standard histological methods to verify that a complete epidermis had, indeed, been produced. The conditions of the binding assay were as follows: Phase III culture medium was aseptically removed and to the reformed human epidermis in each well 0.5 ml of CCS containing 10 to 50 nmol of radiolabelled 17-beta-estradiol (160 Ci/mM;0.2 µCi/ml) was added. The radiolabelled estradiol was purchased from New England Nuclear Corporation, Boston, Mass. The concentration of radiolabelled estradiol was fixed at half maximal saturation to assure effective competition with unlabelled identical and analogue steroid hormones over a wide range of competitor concentrations. The sex steroid competitors tested in tile competition binding assay were 17-β-estradiol and other analogues such as testosterone, estriol, levonorgestral and norethisterone. At the end of the 20 hour incubation interval (at 4° C.) the radiolabelled solutions were removed, the surface of the reformed human epidermis samples rinsed gently with 1 ml of ice-cold CCS and 0.5 ml of Type IV collagenase (Dispase, 20 U/ml, Boehringer-Manheim, Los Angeles, Calif.) added to each well to enzymatically release the intact epidermal sheet. The released reformed human epidermis from each treatment well was transferred to its respective vial and the contained radioactivity was counted in a scintillation spectrometer.

Only 17-β-estradiol was an efficient competitor for the 17-β-estradiol receptor. Estriol, a close structural analog of estradiol also showed significant competition while testosterone and the progesterone analogues were not competitive. These results demonstrate that reformed human epidermis produced as intact epidermal sheets is a good model for biochemical assay of steroid sex hormone receptors and the results also provide direct evidence for the functional fidelity of reformed human epidermis as a living skin substitute.

INDUSTRIAL AND CLINICAL APPLICABILITY

The following claims are based on the five disclosures presented above in Examples 1 through 5. They include the design and formulation of the novel HECK 109 mediums which have been differently supplemented to provide for the serial achievement of the three-step cellular differentiation process of pluripotent, basal cell keratinocytes to a fully differentiated human skin in vitro: i) HECK-109, the basal medium for cell starting; ii) HECK-109-fully supplemented (hereinafter referred to as HECK-109FS) for control over cellular growth; iii) HECK-109-differentiation medium (hereinafter referred to HECK-109DM) for the induction of differentiation and formation of a Malphigian layer and iv) HECK-109-cornification medium (hereinafter referred to HECK-109CM) designed for the induction of cellular differentiation of a stratum lucidum, stratum corneum, and stratum disjunction in a pre-existing reformed epidermis produced by HECK-DM. The fifth and sixth claims involve the process for the sequential rendering of the culture process steps and the method of sequential control in the in vitro construction of a histologically-complete living skin substitute. These media and processes have application in in vitro testing of pharmaceuticals and topical drugs; screening of toxicants, carcinogens, complete or incomplete tumor promoters; evaluation of infective human agents including viruses, e.g. human papilloma viruses, Herpes-simplex viruses and Epstein-Barr virus; screening of cosmetics; production of keratinocyte products including protease inhibitors, growth factors, wound-healing factors, e.g. α-, β-TGF and α-EGF, low-density lipoprotein receptors, laminins, fibronectins, retinoid receptors and binding proteins, steroid hormone receptors, transglutaminases, and cross-linking proteins of the cornified envelope; products for the abolition and/or prevention of wrinkles or screening of agents with potential for prevention of wrinkles; products for use in the introduction of immunizing agents into the recipient a reformed human epidermis graft or evaluation of cross-typing of donor-recipient tissues; and the use of autologously-derived cells for transplantation in the treatment of burns or other trauma.

I claim:

1. An aqueous solution for isolating keratinocytes from human skin, said solution consisting essentially of:
   a) glucose at a concentration of about 10 mM;
   b) N-(2-OH-ethyl-) piperazine -N'-(2-ethanesulfonic acid) at a concentration of 16–22 mM;
   c) sodium chloride at a concentration of 90–140 mM;
   d) potassium chloride at a concentration of about 3 mM;
   e) sodium orthophosphate ($Na_2HPO_4 \cdot 7H_2O$) at a concentration of 1 mM;
   f) phenol red at a concentration of 0.0033 mM;
   g) about 100 units of penicillin per ml of solution;
   h) about 100 units of streptomycin per ml of solution; and
   i) one component selected from the group consisting of:
      (i) trypsin at a concentration of 0.1%–0.2% w/v; and
      (ii) soy bean trypsin inhibitor at a concentration of 0.1–1.0% w/v.

2. The solution of claim 1 wherein said component is soy bean trypsin inhibitor.

3. A method for the isolation of basal epidermal keratinocytes from human skin, said method comprising the steps of:
   a) obtaining human skin;
   b) comminuting said skin;
   c) placing said comminuted skin in a solution consisting essentially of:
      i) glucose at a concentration of about 10 mM
      ii) N-(2-OH-ethyl-)piperazine-N'-(2-ethanesulfonic acid) at a concentration of about 16–22 mM
      iii) sodium chloride at a concentration of about 90–140 mM;
      iv) potassium chloride at a concentration of about 3 mM;
      v) sodium orthophosphate at a concentration of about 1 mM;
      vi) phenol red at a concentration of about 0.0033 mM;
      vii) about 100 units of penicillin per mL of solution;
      viii) about 100 units of streptomycin per mL of solution; and
      ix) trypsin at a concentration of 0.1%–0.2% w/v
   at a temperature and for a time sufficient to allow separation of the dermis from the epidermis;
   d) collecting said epidermis; and
   e) collecting said basal keratinocytes from said epidermis in a solution consisting essentially of:
      i) glucose at a concentration of about 10 mM
      ii) N-(2-OH-ethyl-)piperazine-N'-(2-ethanesulfonic acid) at a concentration of about 16–22 mM
      iii) sodium chloride at a concentration of about 90–140 mM;
      iv) potassium chloride at a concentration of about 3 mM;
      v) sodium orthophosphate at a concentration of about 1 mM;
      vi) phenol red at a concentration of about 0.0033 mM;
      vii) about 100 units of penicillin per mL of solution;
      viii) about 100 units of streptomycin per mL of solution; and
      ix) soy bean trypsin at a concentration of 0.1%–1.0% w/v.

4. The method of claim 3 wherein said
   a) sodium chloride is a concentration of about 100–130 mM;
   b) N-(2-OH-ethyl-)piperazine-N'-(2-ethanesulfonic acid) is at a concentration of about 18–21 mM;
   c) trypsin is at a concentration of 0.1%–0.18% w/v; and
   d) soy bean trypsin inhibitor at a concentration of 0.3%–0.8% w/v.

5. The method of claim 3 wherein said step (c) is conducted for 14–16 hours at a temperature of 4° C.

6. The solution of claim 1 wherein said component is trypsin.

7. The solution of claim 1 wherein said:
   a) sodium chloride is at a concentration of 100–130 mM;
   b) N-(2-OH-ethyl-) piperazine-N'-(2-ethanesulfonic acid) is at a concentration of 18–21 mM;
   c) trypsin is at a concentration of 0.12–0.18% w/v; and
   d) soy bean trypsin inhibitor is at a concentration of 0.3–0.8% w/v.

* * * * *

UNITED STATES PATENT AND TRADEMARK OFFICE
CERTIFICATE OF CORRECTION

PATENT NO. : 5,795,781
DATED : August 18, 1998
INVENTOR(S) : John J. Wille, Jr.

It is certified that error appears in the above-identified patent and that said Letters Patent is hereby corrected as shown below:

In column 1, line 44, please delete the word "$Ca^{24}$" and replace it with -- $Ca^{2+}$ --.

In column 3, line 30, please delete the equation "$5.0 \times 10^-_4 M$", and replace it with -- $5.0 \times 10^{-4} M$ --.

In column 8, lines 5 and 6, please delete the number "$10^-_4 M$", and replace it with -- $10^{-4} M$ --.

In column 8, lines 6 and 7, please delete the number "$10^-_4 M$", and replace it with -- $10^{-4} M$ --.

In column 13, line 52, please delete the word "tile", and replace it with -- the --.

Signed and Sealed this

Twelfth Day of January, 1999

Attest:

Attesting Officer

*Acting Commissioner of Patents and Trademarks*